(12) United States Patent
Karle (10) Patent No.: US 7,189,349 B2
(45) Date of Patent: Mar. 13, 2007

(54) FLEXIBLE WALK-IN ENVIRONMENTAL ENCLOSURE

(75) Inventor: David A. Karle, Girard, PA (US)

(73) Assignee: Steris Inc, Temecula, CA (US)

( * ) Notice: Subject to any disclaimer, the term of this patent is extended or adjusted under 35 U.S.C. 154(b) by 613 days.

(21) Appl. No.: 10/345,743

(22) Filed: Jan. 16, 2003

(65) Prior Publication Data

US 2003/0133834 A1 Jul. 17, 2003

Related U.S. Application Data

(60) Provisional application No. 60/349,046, filed on Jan. 16, 2002.

(51) Int. Cl.
*A61L 2/20* (2006.01)
(52) U.S. Cl. .................. 422/28; 422/32; 422/294; 135/96
(58) Field of Classification Search ............... 422/294, 422/32; 52/2.14
See application file for complete search history.

(56) References Cited

U.S. PATENT DOCUMENTS

| | | | | |
|---|---|---|---|---|
| 1,817,536 A * | 8/1931 | Spanel | ............... | 422/294 |
| 4,026,286 A * | 5/1977 | Trexler | ............... | 128/205.26 |
| 4,169,123 A | 9/1979 | Moore et al. | | |
| 4,461,097 A * | 7/1984 | Thornton | ............... | 34/233 |
| 4,706,551 A * | 11/1987 | Schofield | ............... | 454/66 |
| 4,885,000 A * | 12/1989 | Hogan | ............... | 600/21 |
| 4,909,999 A | 3/1990 | Cummings et al. | | |
| 4,949,863 A * | 8/1990 | Cazalis et al. | ............... | 220/9.1 |
| 5,068,087 A | 11/1991 | Childers | | |
| 5,173,258 A | 12/1992 | Childers | | |
| 5,258,162 A | 11/1993 | Andersson et al. | | |
| 5,779,973 A | 7/1998 | Edwards et al. | | |
| 5,788,925 A | 8/1998 | Pai et al. | | |
| 5,792,435 A | 8/1998 | Mueller et al. | | |
| 6,145,525 A * | 11/2000 | Mooney | ............... | 135/119 |
| 6,192,633 B1 * | 2/2001 | Hilbert | ............... | 52/2.18 |
| 6,235,240 B1 * | 5/2001 | Heredia et al. | ............... | 422/30 |
| 2003/0037812 A1* | 2/2003 | Stewart et al. | ............... | 135/96 |
| 2003/0074845 A1* | 4/2003 | Sample et al. | ............... | 52/63 |

FOREIGN PATENT DOCUMENTS

DE 19540564 A1 * 5/1997

* cited by examiner

*Primary Examiner*—E. Leigh McKane
(74) *Attorney, Agent, or Firm*—Fay Sharpe LLP (57) ABSTRACT

An enclosure assembly (10, 10, 10) includes a framework (12) formed from structural members and a flexible transparent enclosure (14) which provides an enclosed space for isolation and or treatment of patients, equipment, and the like. A treatment material, such as hydrogen peroxide or other gaseous or vapor sterilant, may be fed to the enclosure to microbially decontaminate or otherwise treat the equipment. The enclosure is quickly assembled and disassembled after use, making it suitable for treatment of large pieces of equipment which are not readily moved or which are too large to be accommodated conventional sterilization equipment.

34 Claims, 6 Drawing Sheets

Fig. 6

FLEXIBLE WALK-IN ENVIRONMENTAL ENCLOSURE

This application claims the priority of U.S. application Ser. No. 60/349,046, filed on Jan. 16, 2002, which is incorporated herein in its entirety, by reference.

BACKGROUND OF THE INVENTION

The present invention relates to the field of environmental decontamination. It finds particular application in conjunction with a portable enclosure for microbial decontamination of large pieces of equipment, and will be described with particular reference thereto. It should be appreciated, however, that the invention is also applicable to the decontamination, treatment, or isolation of other items, both large and small.

Small pieces of equipment used in medical, pharmaceutical, food, and other applications are frequently sterilized or otherwise microbially decontaminated prior to use or reuse. Concerns arise, however, when larger pieces of equipment, such as food and pharmaceutical processing equipment, mail handling equipment, and the like become contaminated with harmful organisms or other species. Such equipment is often too large or is unsuited to being transported to a decontamination system, such as a sterilizer. Further, there is often concern that transporting the contaminated equipment around a facility or to an offsite decontamination system may pose hazards to those transporting the equipment or may spread the contamination around the facility or to transportation equipment.

The present invention provides a new and improved portable environmental enclosure and method of use which overcome the above-referenced problems and others.

SUMMARY OF THE INVENTION

In accordance with one aspect of the present invention, a method of isolating and treating an item is provided. The method includes enclosing the item in an enclosure assembly which includes assembling a framework and hanging a flexible enclosure on the framework. The flexible enclosure defines, at least in part, an enclosed space. At least one fluid supply passage is connected with the enclosure for supplying a treatment fluid thereto. The item is isolated within the enclosed space. The fluid supply passage is connected with a source of the treatment fluid. The treatment fluid is supplied to the enclosed space to treat the item.

In accordance with another aspect of the present invention, a walk-in enclosure assembly is provided. The assembly includes a framework. A flexible enclosure is hung on the framework which defines, at least in part, a substantially airtight enclosed space. A fluid supply passage is fluidly connected with the enclosed space for supplying the enclosed space with a microbial decontaminant.

In accordance with another aspect of the present invention, a decontaminant system is provided. The system includes a portable framework and a flexible enclosure hung on the framework which defines, at least in part, an enclosed space. A fluid flowpath fluidly connects a source of microbial decontaminant with the enclosed space for supplying the enclosed space with a decontaminant fluid.

One advantage of the present invention is that items which are immovable may be readily isolated or sterilized.

Another advantage of the present invention is that equipment which is contaminated may be isolated without moving the equipment to a separate isolation area.

Another advantage resides in its thermal control of the isolated environment.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
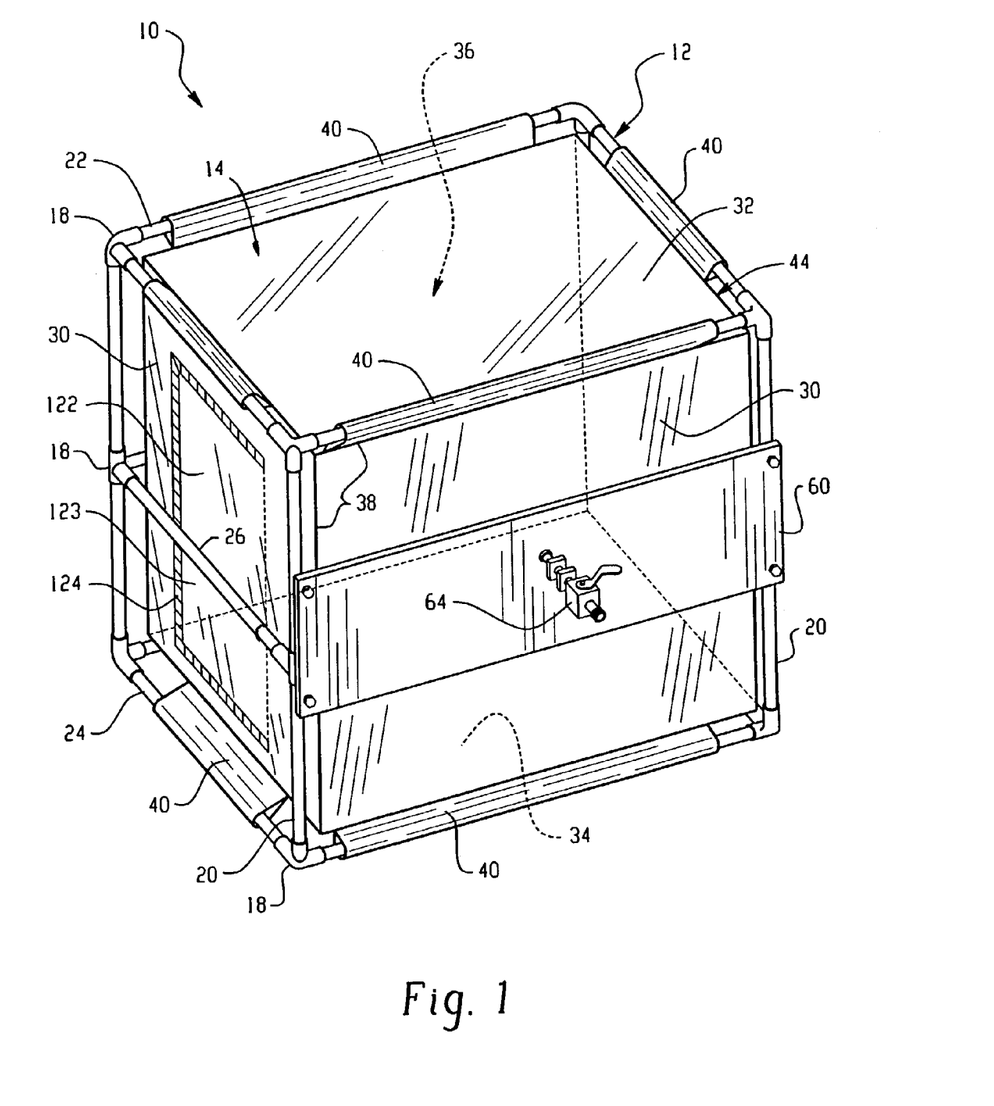
FIG. 1 is a perspective view of an environmental enclosure according to the present invention.

With reference to FIG. 1, a portable enclosure assembly 10 is suitable for temporarily isolating and/or treating equipment. The enclosure is readily erected or placed around the equipment to isolate the equipment for a treatment process, such as gaseous decontamination process, for example, with vapor hydrogen peroxide or other gaseous sterilant. The enclosure assembly 10 is also suited to isolating a patient having a communicable disease or who is otherwise contaminated or for protecting people from an exterior hazardous environment. Equipment which can be isolated or treated in the enclosure includes food and beverage processing equipment, such as cooking, processing, chilling, slicing, packaging and bottling equipment which may be contaminated by food or airborne microorganisms and/or other potentially harmful species. Other equipment can also be treated, such as medical and veterinary equipment contaminated with body fluids or other sources of microorganisms, including beds, chairs, washing facilities, and the like. Pharmaceutical processing equipment, mail-handling equipment, and other equipment may be isolated and/or treated. Equipment is isolated and treated without moving the equipment to an isolation site, reducing the chance that harmful microorganisms will be spread around a facility. Additionally, some equipment which is too heavy or too large convenient movement can be cleaned in place.

The enclosure assembly 10 is configured for treatment processes, particularly microbial decontamination processes, such as sterilization or lesser forms of decontamination, including disinfection and sanitization, but other processes are also contemplated.

The assembly 10 includes an exterior framework 12, and a flexible enclosure or tent 14, which is supported by the framework. The framework is formed from elongate rigid members, such as poles 16, which may be hollow tubes or solid members, and interconnecting pieces or elbows 18, which allow the framework 12 to be readily assembled and then disassembled when no longer required. The poles 16 and interconnecting pieces 18 are preferably formed of aluminum or other suitable lightweight material. The framework 12 is suitably sized to surround a piece of equipment to be decontaminated or to provide a room which allows isolation of a patient or the like. For example, the framework 12 is 2–5 meters in each dimension.

The framework 12 shown in FIG. 1 is assembled from horizontally and vertically oriented members 16. For example, the framework 12 includes four generally vertical corner members, such as poles 20, four upper horizontal members, such as poles 22, and four lower horizontal members, such poles 24, which together define the shape of a cube or other six-sided rectangular structure. Four or more horizontal bracing members, such as poles 26 are mounted between the adjacent vertical poles 20 by suitable interconnecting pieces 18. Similarly, for larger room structures, additional intermediate vertical poles (not shown) are provided between pairs of vertical poles 20. Diagonal and other bracing arrangements are also contemplated. It will be appreciated that the framework 12 is not limited to six sides but can have any number of sides depending on the desired size and shape of the item or items to be enclosed.

The enclosure 14 is preferably formed from a flexible transparent sheet material, which is airtight, such as vinyl, and is sized to fit in the space provided by the framework 12. Preferably, the enclosure is slightly smaller than the framework and is suspended inside of it. A suitable vinyl is about 15–25 gauge, preferably about 19 gauge. The enclosure 14 shown in FIG. 1 is formed from panels, specifically, four side panels 30, a roof panel 32, and a floor panel 34. The panels 30, 32, 34 are sealed together at their edges to define an enclosed space 36 which is preferably airtight, or substantially airtight. By substantially airtight it is meant that if air at a pressure equivalent to 1.5" (about 3.81 cm) water is supplied to the enclosure 14 and allowed to equilibrate for 2 minutes, and then the air pressure supply is disconnected, the pressure within the enclosure after a further 5 minutes is at least 0.8" (about 2 cm) water, more preferably, at least about 1.0" water (2.54 cm). The enclosure 14 may be leak tested, prior to use, to check that the enclosure is substantially airtight, for example, by pressurizing the enclosure to about 1.5 cm water, equilibrating for 1 minute, and testing to ensure that an acceptable pressure level is maintained, such as a pressure of 1.0 cm after 2 minutes Seams 38 are preferably double lapped and sewn, adhesively joined, thermally fused together, or the like.

The flexible enclosure 14 is suspended from the upper horizontal poles 22 and anchored to the lower horizontal poles 24 by tabs or loops 40, which are looped over a respective horizontal pole. The tabs 40 keep the enclosure 14 relatively taut when the enclosure assembly 10 is fully assembled to provide the enclosed space 36. While a single elongated tab 40 is shown for each horizontal pole 22, 24 it will be appreciated that more than one tab or other suspension and anchoring mechanisms may be provided.

The enclosure assembly 10 of FIG. 1 is particularly suited to treatment of items which can be transported, for example on a wheeled cart or conveyor, into the enclosure 12. Food and beverage items, packaging materials, medical appliances, vehicles, mail, and the like are readily treated in the enclosure 10.

Figure 2:
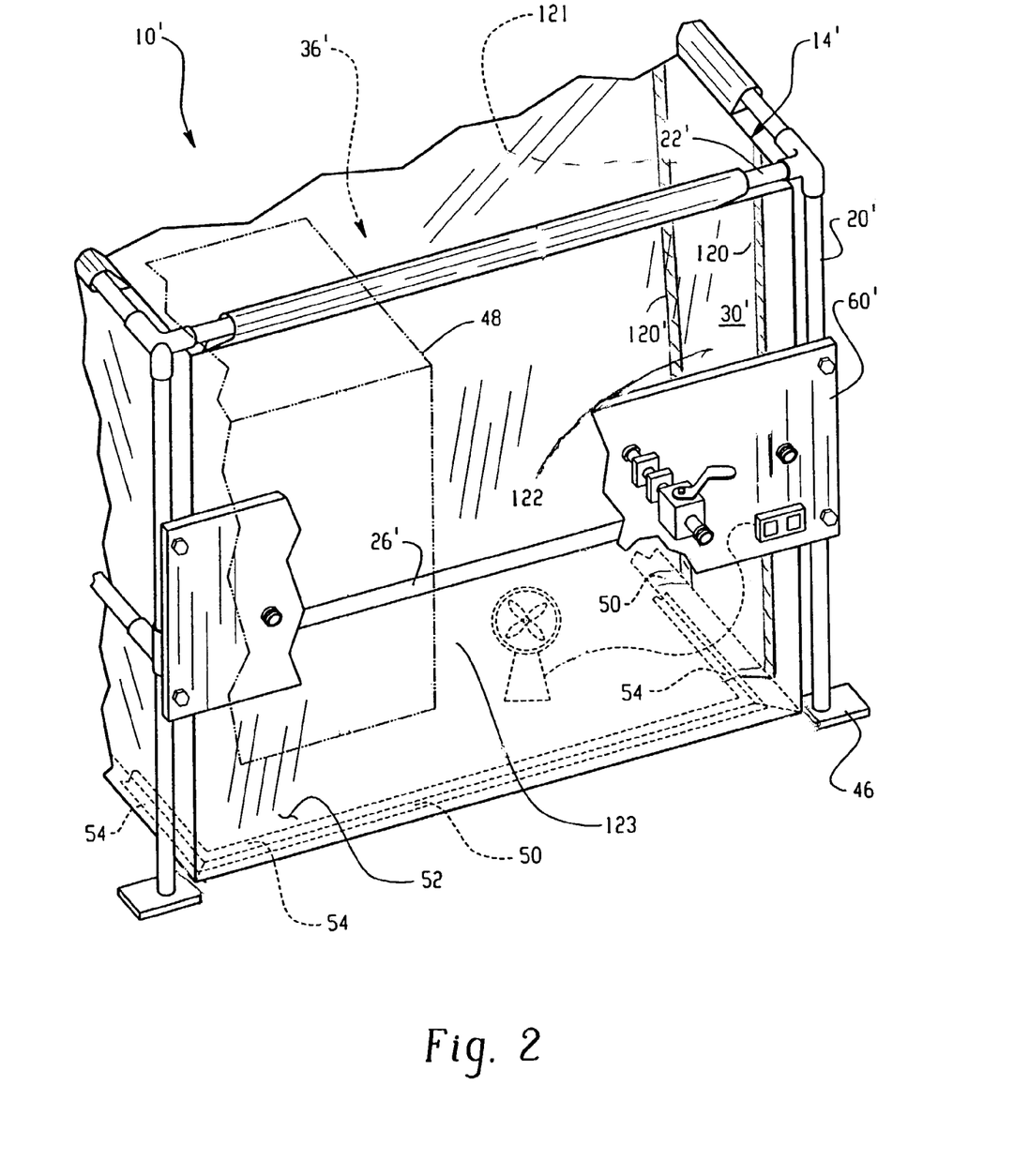
FIG. 2 is a perspective view of a wall of second embodiment of an environmental enclosure according to the present invention.

With reference now to FIG. 2, a second embodiment of an enclosure assembly 10' is formed without a floor panel and, optionally, without lower horizontal members. The enclosure assembly is similar to the embodiment of FIG. 1. Like components are given the same numerals, designated by a prime (') while new elements are given new numerals.

Figure 3:
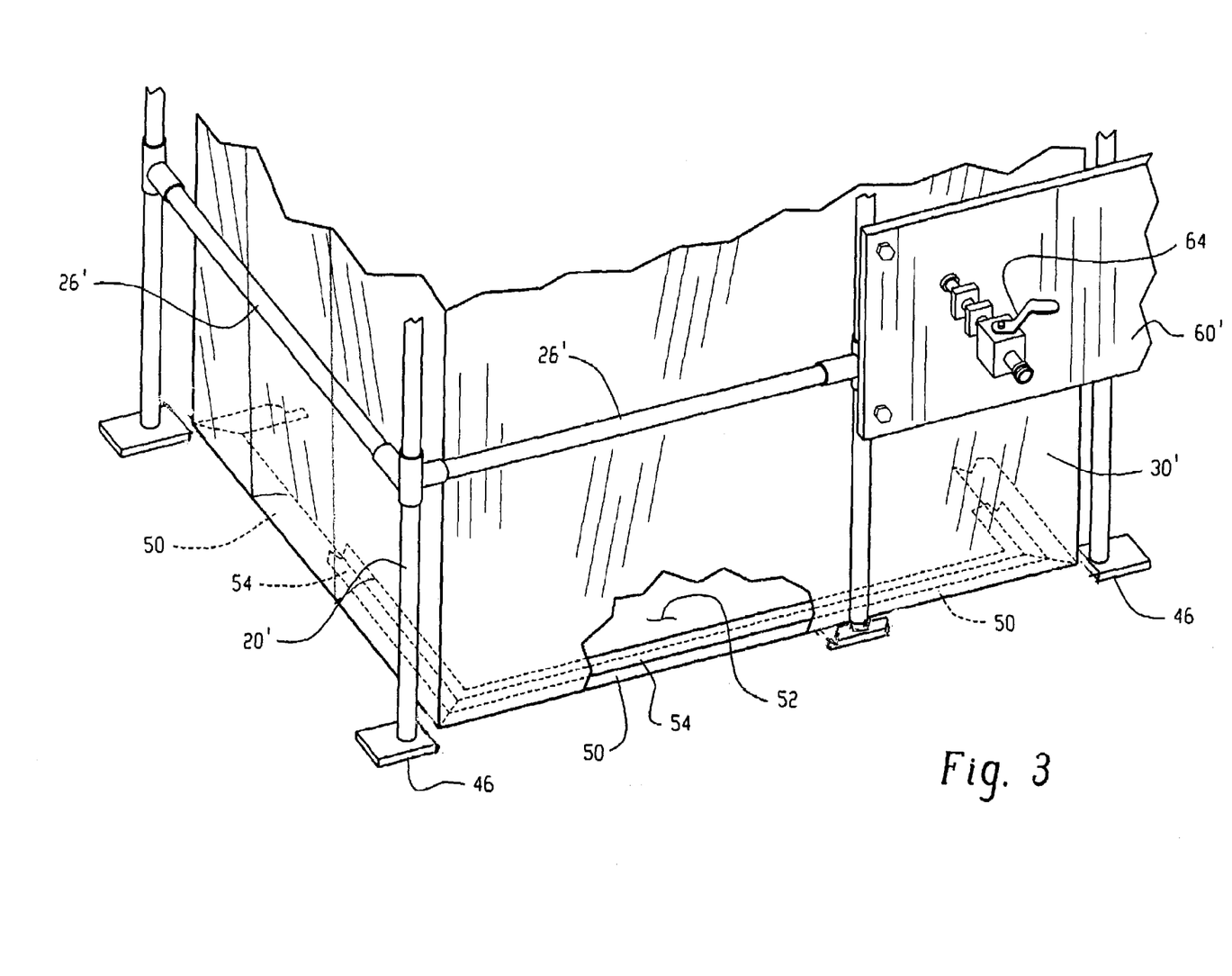
FIG. 3 is a perspective view of a portion of the enclosure of FIG. 2.

With reference also to FIG. 3, the enclosure assembly 10 has a framework 12' which includes four upper horizontal members 22', four vertical corner members 20', and optionally additional bracing members 26. Plates 46, which are welded or otherwise attached to a lower end of each vertical corner member 20', are provided for mounting the framework 12' to the floor or for resting it thereon.

The enclosure assembly 10' of FIGS. 2 and 3 is suited to enclosing a piece of equipment 48 or other structure which is mounted to the floor or which is not readily transported into an enclosure such as that of FIG. 1. The framework 12' is thus preferably constructed around the equipment 48, or other item to be enclosed, and the enclosure 14' hung over the item. Alternatively, the entire enclosure assembly 10' can be lowered over the equipment from above.

In this embodiment, flaps 50 are provided at the lower ends of each of the side panels 30'. These can be extensions of the panels 30' and formed from the same material. The flaps 50 are configured for resting on the adjacent floor surface 52 on which the enclosure assembly is erected. The edges of the flaps are taped to the floor using duct tape 54 or similar removable tape or other adhering medium to provide a substantially airtight enclosed space 36' by forming a seal between the enclosure and the floor 52. For this purpose, the floor 52, or other surface on which the enclosure is erected, is smooth, or substantially smooth, and is formed from a non-porous material. In the embodiment shown in FIG. 2, the flaps are turned inward, into the enclosed space 36' within the enclosure 14'. This embodiment is generally preferred when the enclosure 14' is to be maintained at an above atmospheric pressure during operation. For instances in which the enclosure 14' is to be maintained at below atmospheric pressure, the flaps 50 are preferably turned outward, away from the enclosure 14' and the tape 54 applied outside the enclosure.

As shown in FIG. 3, the walls 30', 32' of the enclosure 14, 14' may be formed from two or more separate wall panels (e.g., 30A and 30B), which are joined at seams 56. Optionally, corner reinforcements are provided for extended life.

Figure 4:
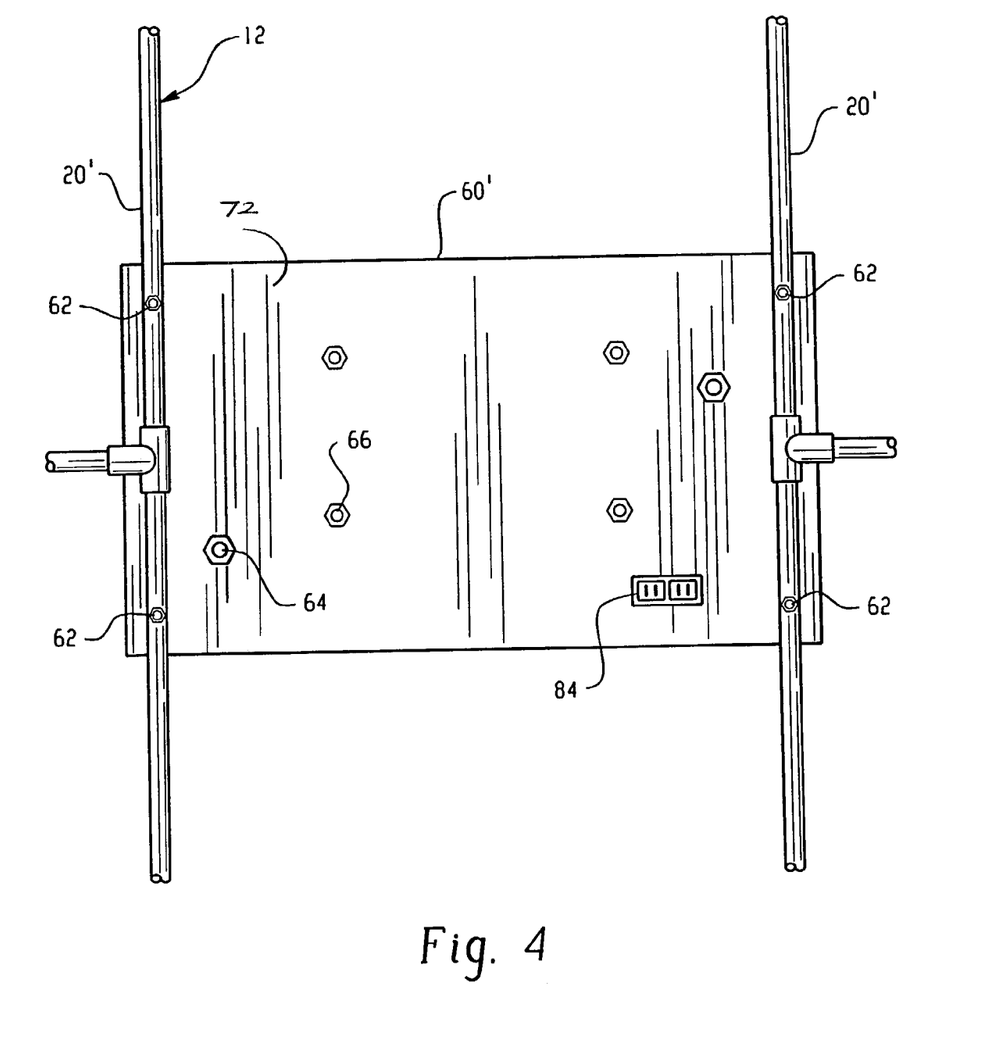
FIG. 4 is an enlarged view of the control panel of FIG. 2.
Figure 5:
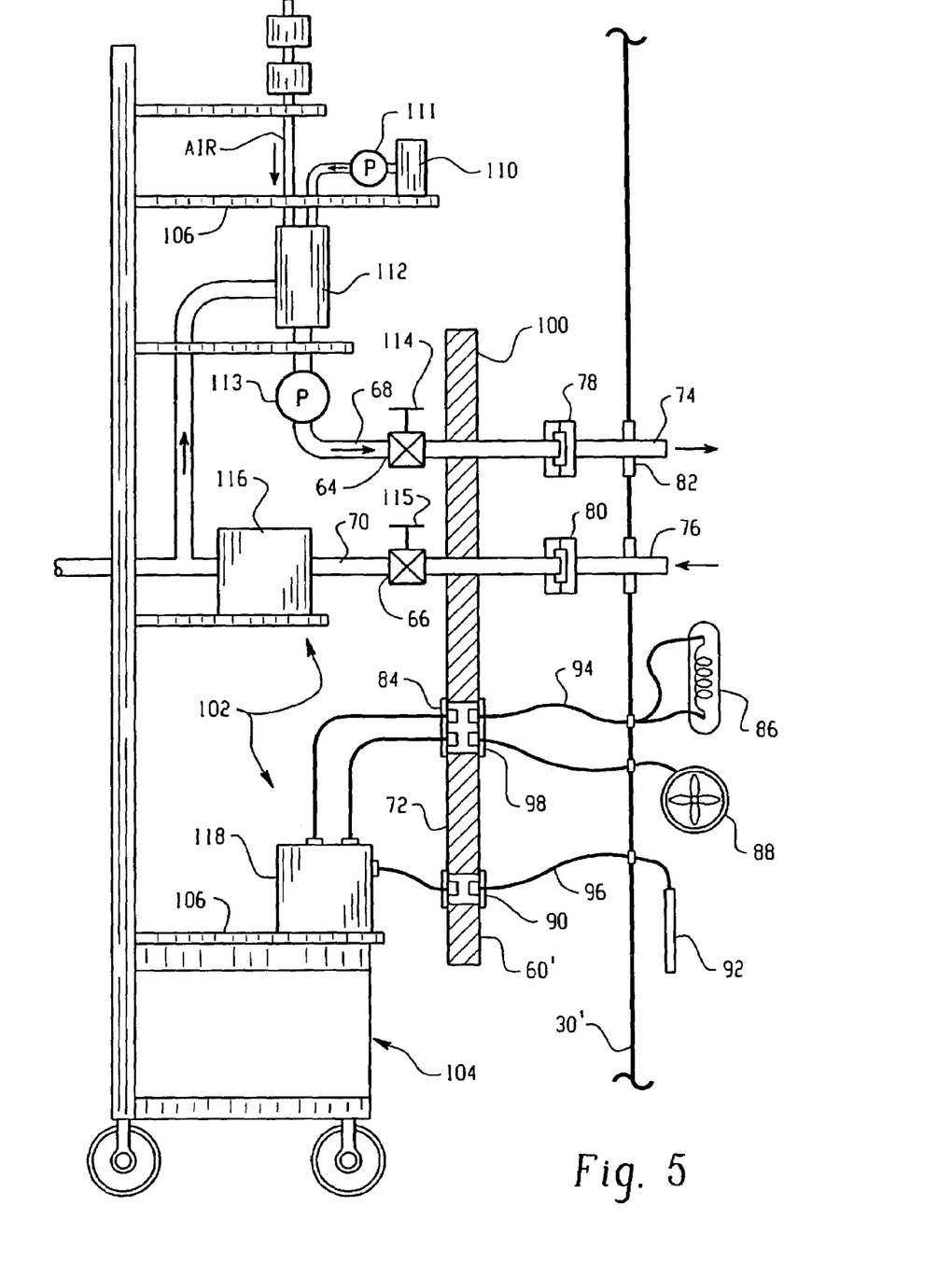
FIG. 5 is a side view of the control panel of FIG. 2 and a portable equipment cart.

A rigid support panel in the form of a plate or multiple plates 60, 60' is/are mounted to the framework 12, 12' of either embodiment for providing gas, electric, and other connections between the exterior of the enclosure and the interior space. As shown in FIG. 4, the plate 60' is mounted to two adjacent vertical members 20' by bolts 62, or other suitable fixing members. With reference also to FIG. 5, suitable ports 64, 66, which provide connectors for selective connection with gas inlet and outlet conduits, such as tubes 68, 70, respectively, are provided on a front face 72 of the plate 60'. The ports 64, 66 are connected with fluid passages, such as tubes 74, 76, which pass through a side panel 30' of the enclosure 14', thereby providing fluid flowpaths into and out of the enclosure. As shown in FIG. 5, quick connects 78, 80 may be provided for quickly connecting and disconnecting the fluid passages 74, 76 from the plate 60. The fluid passages 74, 76 pass through openings in the enclosure wall 30' and are sealed around their exteriors to the adjacent wall surface by suitable sealing members 82. In one embodiment, grommets, flap valves, gaskets, or the like sealingly engage individual passages. In another embodiment, the side panel 30, 30' is sealed permanently or releasably to the plate 60'. For example, in one embodiment, the side panel 30' has an opening (not shown) just smaller than the rigid plate 60'. An adhesive, magnetic, or other seal extends around the periphery of the opening to seal the side panel to the plate.

The plate 60, 60' also supports electrical connections 84, such as an electrical socket or sockets for connecting a source of electrical power (not shown) with equipment within the enclosure 14, 14, such as one or more heaters 86 and one or more circulation fans 88, lights, electrical equipment, and the like. Connectors 90 for connecting exterior monitoring equipment with sensors 92 within the enclosure are also provided on the plate 60, 60'. Such connections 90 may include connections to temperature and humidity sensors, chemical sensors, and the like. Two or more of each of the sensors, 92 are preferably disposed around the enclosed space 36' for determining maximum and minimum values. As with the fluid connections, electrical and sensor wiring 94, 96 is quickly connectable to and disconnectable from the plate 60, 60' for example, by providing suitable electrical sockets 98 on a rear surface 100 of the plate.

As shown in FIG. 5, supporting equipment 102 for maintaining and monitoring the environment within the enclosure 14, 14 is preferably mounted on a wheeled cart 104, which is positioned, when needed, adjacent the plate 60, 60'. The various maintaining and monitoring equipment 102 is advantageously mounted on suitable shelves 106 of the cart.

The equipment 102 illustrated in FIG. 5 is exemplary of a system for supplying and monitoring a vapor hydrogen peroxide decontaminant or similar gaseous or vapor decontaminant. It will be appreciated that a variety of gaseous decontaminants are alternatively contemplated, such as vapor peracids, e.g, peracetic acid, gaseous sterilants, such as ethylene oxide, and the like. Alternatively, the enclosure 14, 14' is used to control escape of hazardous agents from the equipment 48 into the surrounding air or to enclose the equipment during another treatment process.

As shown in FIG. 5, a suitable system 102 for supplying and monitoring vapor hydrogen peroxide introduction and decontamination includes a source 110 of liquid hydrogen peroxide in solution, such as a reservoir of aqueous hydrogen peroxide at a concentration of about 20–40% by weight hydrogen peroxide. The hydrogen peroxide liquid is fed by a pump 111 into a vaporizer 112, where the hydrogen peroxide and water components are vaporized on a heated surface (not shown). The vapor is carried in a carrier gas, such as air or other flow medium from a source of carrier gas, such as a pump or pressurized reservoir, along the supply conduit 68 to the inlet port 64 using a pump 113. Valves 114, 115 in the inlet and outlet ports 64, 66, respectively, are used to regulate the inflow of vapor to the enclosure 14 and outflow of spent vapor. Several inlet ports 64 are preferably provided for supplying different areas of the enclosure space 36. The spent vapor exits the enclosure 14 through the outlet line 70 and port 66 and is advantageously transported to a catalytic converter 116 or other destroyer before being released to the atmosphere. Alternatively, all or a portion of the vapor is recirculated through the vaporizer 112. A control system 118 includes monitoring equipment which receives information from the sensors 92, such as temperature, humidity, and hydrogen peroxide concentration. The control system uses the information to control variables, such as the rate of hydrogen peroxide vaporization, the carrier gas flow rate, the temperature of the heater 86, and other operating parameters in order to maintain desired conditions for microbial decontamination within the enclosure.

Hydrogen peroxide is a particularly effective decontaminant for many air and food borne microbes and other toxic materials, including bacteria, fungi, yeasts, and prions. The spores responsible for Anthrax and other microbial contamination, for example, are readily destroyed using a short exposure period of a few minutes. Chemical contaminants may also be treated with a decontaminant gas or vapor, or with another treatment, such as UV radiation, or the like.

Prior to introducing the vapor, a slight negative pressure is preferably applied to the enclosure 14, 14', to speed up the introduction and dispersal of the vapor.

The enclosure 14, 14' is capable of maintaining an interior pressure which is slightly above atmospheric pressure or slightly below atmospheric pressure. Below atmospheric pressures are preferred when it is desirable to minimize any leakage of airborne contaminants from the enclosure. Preferably, for vapor hydrogen peroxide decontamination, the enclosure is able to withstand approximately three times a normal operating pressure of 2–5 cm of water to provide a margin of safety.

With reference once more to FIG. 2, access to the enclosure 14' is provided by a closure member, preferably a zipper or zippers 120, which provide a resealable opening 121 into the enclosure. The zipper 120 is preferably of the type which allows an airtight or substantially airtight seal to be maintained, such as a rail seal type zipper. A suitable zipper is YKK, Inc.'s model No. 8RS-PVC40 (YKK, Inc., Springfield, Pa.). As shown in FIG. 2, two vertical zippers 120, 120' are preferably provided at left and right sides of the opening, respectively. The vinyl door 122 panel thus formed between the two zippers is rolled upward to allow access to the enclosure 14'. The door has its own flap 123, which can be held down by tape, as for the wall panel flaps 50. Alternatively, as illustrated in FIG. 1, a single zipper 124 provides three sides of a door. As illustrated, the zipper 124 runs along a lower end of the opening turns, and runs vertically up to the top of the opening and then runs along the top of the opening. The wall panel is sufficiently flexible to allow the door 122 thus created to open. The horizontal bracing members 26 may be removed or left off in the area of the door. In another embodiment, the bracing member is hinged on one side and has a button released snap lock on the other to swing open like a gate.

Figure 6:
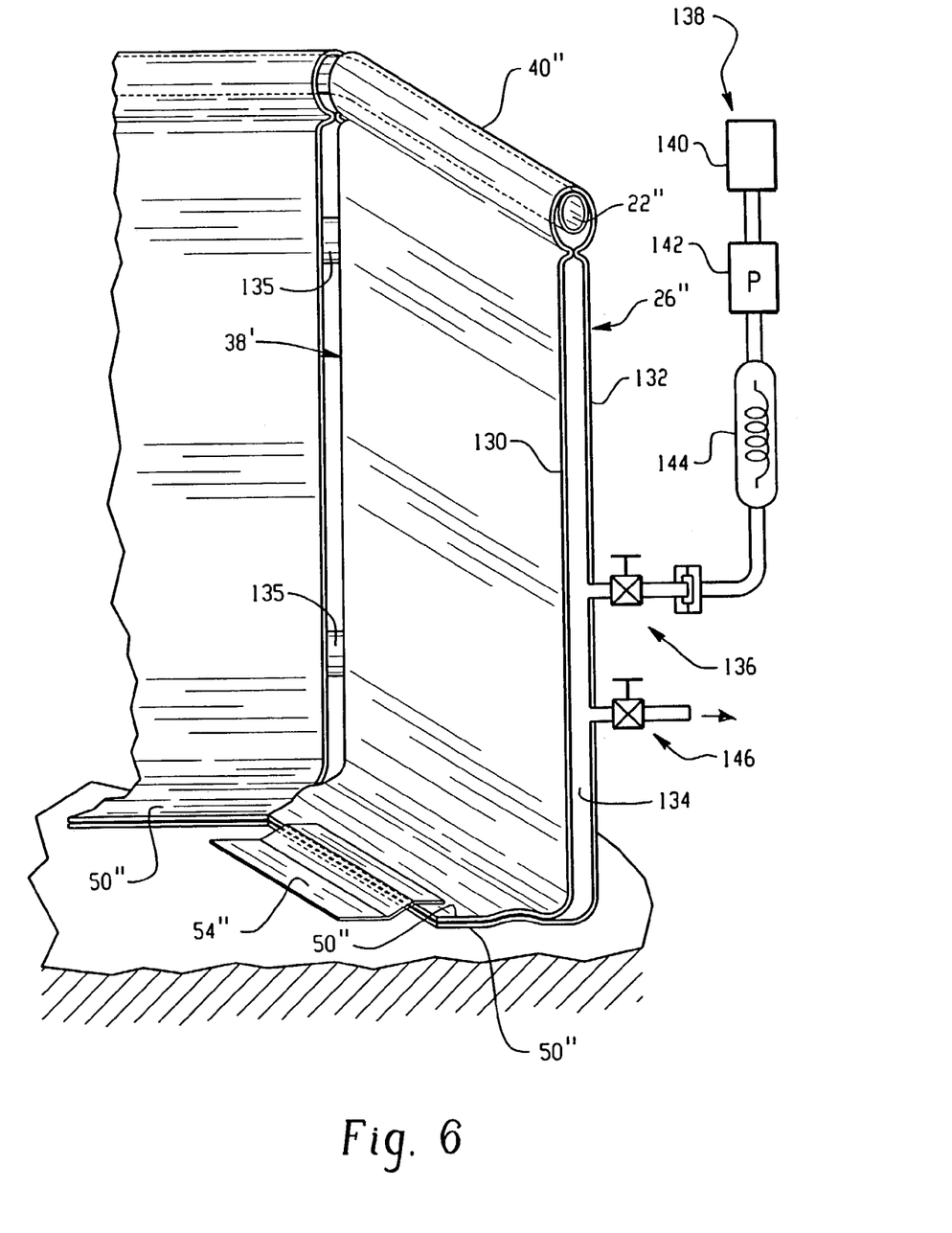
FIG. 6 is a side view of a third embodiment of an environmental enclosure according to the present invention.

With reference now to FIG. 6 an alternative embodiment of an enclosure assembly 10", where like elements are denoted by a double prime ("), has walls 30" formed from inner and outer layers 130, 132 of vinyl, or other transparent material. The assembly 10" may be analogous to assembly 10 or 10' in other respects. The inner layer 130 is suspended inside the outer layer 132 and sealed thereto at upper and lower ends to provide an enclosed wall space 134 therebetween. The enclosed space 134 which can be heated or cooled to maintain a desired temperature within the enclosure 14". At the top and side corners, tabs 133 with air passages support the inner wall 130 and maintain the spacing. Each of the walls 30", and also the ceiling panel 32", and door panel 122" are preferably double walled. In one embodiment, each panel provides a separate enclosed wall space 134. Alternatively, the enclosed spaces 134 in the walls and ceiling are interconnected by fluid passages 135 which allow air to flow between the enclosed spaces and equalize in pressure. The enclosed wall space 134 is inflated by supplying it with air or other fluid under a slight positive pressure. For this purpose, an inlet valve 136 is selectively connected with a source 138 of air (which can be the same as the source of carrier gas, or a different source), such as a pressurized cylinder 140 or a pump or compressor 142. The air is supplied to the inlet valve 136 under slight positive pressure via a temperature element, such as a heating or cooling element 144. For hydrogen peroxide or other vapor or gaseous sterilization processes, the temperature element 144 is preferably a heating element, which heats the incoming air to a suitable temperature for maintaining the enclosure 14" at an optimal temperature for microbial decontamination and to prevent condensation on the walls. An outlet valve 146 provides for release of the air from the enclosed wall space 134 the end of a treatment process and optionally allows the air to slowly bleed from the enclosed space 36" to allow the enclosed wall space to be supplied with additional heated air, if desired. Flaps 50" are readily formed by sealing the inner and outer wall layers 130, 132 together at their lower ends.

In an alternative embodiment, heating elements, such as heat lamps (not shown) are placed around the exterior of the enclosure 10, 10', 10" to heat the walls and the interior space.

To assemble the enclosure assembly 10', 10", the framework 12', is constructed, preferably around an item to be isolated or treated, or in the case of assembly 10, prior to introduction of the items. The tabs 40, 40', 40" of the enclosure 14, 14', 14" are preferably hung on the upper horizontal members 22, 22', 22" prior to connecting these with the corner connecting members. In the case of the assembly of FIG. 2, the zipper(s) 120 are opened and an operator enters the room to tape the flaps 50 to the floor. The heaters 86, fans 88, and any other equipment for a treatment process are positioned in the enclosed space 36 and connections made to the panel 60, 60' using the quick connects. The zipper(s) 120 are then closed and taping of the door panel flap 123 is carried out, if necessary. The ends of the zipper 120 are also sealed by design of the zipper. In the case of the enclosure of FIG. 6, heated or cooled air at a suitable temperature is supplied to the wall spaces 134. Control equipment and supply and monitoring equipment 102 are positioned adjacent the enclosure assembly and the appropriate connections made via the plate 60, 60'.

A treatment material, such as a vapor or gaseous sterilant, is fed to the enclosed space 36, 36, e.g., at a pressure of about 2–5 cm of water, and maintained in the enclosure for a sufficient period of time to effect the desired treatment process, such as sterilization or disinfection. During the treatment process, conditions within the enclosure are preferably monitored and controlled to maintained desired conditions for treatment. At the end of the treatment process, a slight negative pressure is applied to the enclosure 14, 14' to draw the vapor out of the enclosure and to draw fresh air into the enclosure in its place. Alternatively, the enclosed space 36 is flushed with filtered air. Once a safe atmosphere in the enclosure has been restored, the zipper 120 is opened and the operator enters to remove the tape 54 from the flaps 50. The electrical and fluid connections 78, 80, 98, are disconnected and the lines 68, 70 disconnected from their respective ports 64, 66. The enclosure assembly 10, 10', 10" is then disassembled and moved to another location or placed into storage until needed again. The equipment cart 104 is wheeled away.

It will be appreciated that the enclosure 10, 10', 10" has a variety of other applications, including isolation of potentially contaminated equipment and patients. For such applications, the enclosure may be maintained under a slight negative pressure using a pump or other suitable suction equipment (not shown). Air that is withdrawn from the enclosure through valve 115 is-passed through a filter, such as a HEPA filter (not shown), and any other treatment equipment needed to remove the contamination from the air. The enclosure, being not completely leak tight, allows a small amount of air to slowly leak into the enclosure to replace the withdrawn air, thereby allowing the air quality in the enclosure to be maintained. Alternatively, the inlet valve 114 is cracked open to allow air to bleed into the enclosure to replace the withdrawn air. Inlet air is optionally filtered.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of isolating and treating a stationary piece of equipment in a building or enclosure comprising:
    assembling a framework around the stationary piece of equipment supported on a floor surface of the building or enclosure on which the stationary piece of equipment is supported, the framework being sized to surround the item;
    hanging a flexible enclosure on the framework, the flexible enclosure with the supporting surface defining an enclosed space surrounding the stationary item, at least one gas supply passage being connected with the enclosure for supplying a treatment gas thereto;
    isolating the piece of equipment within the enclosed space;
    sealing the flexible enclosure to the supporting floor surface;
    connecting the gas supply passage with a source of the treatment gas;
    supplying the treatment gas to the enclosed space to treat the piece of equipment; and
    after treating the piece of equipment, removing the flexible enclosure from the framework and disassembling the framework.

2. The method of claim 1, wherein the step of assembling the framework includes connecting together a plurality of elongate members.

3. The method of claim 2, wherein the step of hanging the flexible enclosure on the framework includes:
    suspending the flexible enclosure from upper elongate member by a plurality of tabs.

4. The method of claim 1, further comprising:
    prior to the step of supplying the treatment gas to the enclosure, testing the enclosure to ensure that it is at least substantially airtight.

5. The method of claim 1, wherein the enclosure includes a plurality of flexible panels, joined together at seams.

6. The method of claim 5, wherein at least one of the flexible panels includes a door formed, at least in part, by a rail-type zipper, the method comprising selectively opening the door providing access for a technician to enter and to leave the enclosed space.

7. The method of claim 1, wherein the treatment gas includes an antimicrobial gas or vapor.

8. The method of claim 7, wherein the antimicrobial gas or vapor includes hydrogen peroxide.

9. The method of claim 1, wherein a rigid support panel is mounted to the framework and supports a connector, connected with the gas supply passage, for selectively connecting the gas supply passage with a gas supply conduit which is connected with the source of the treatment gas, the step of connecting the gas supply passage with the source of treatment gas includes selectively connecting the connector with the gas supply conduit.

10. The method of claim 9, wherein the support panel further includes a second connector for connecting a sensor within the enclosure with monitoring equipment, the method further comprising:

selectively connecting the sensor with the monitoring equipment via the second connector; and monitoring environmental conditions within the enclosure with the sensor.

11. The method of claim 1, wherein the flexible enclosure is formed from an airtight material.

12. The method of claim 1, wherein the source of treatment gas includes a vaporizer for converting a liquid to the treatment gas, the method further including:

vaporizing the liquid to form the treatment gas; and
transporting the treatment gas to the enclosure in a flow of a carrier gas.

13. The method of claim 1, wherein the source of treatment gas is supported by a movable cart separate from the framework and the method comprises:

moving the cart from a remote location to a position adjacent the enclosure.

14. The method of claim 13, wherein the cart also supports at least one of:

a source of a carrier gas;
a reservoir of a liquid;
a vaporizer for converting the liquid to the treatment gas;
a pump for pumping the liquid to the vaporizer;
a catalytic converter for decomposing spent treatment gas which has passed through the enclosure;
monitoring equipment for monitoring environmental conditions within the enclosure, the environmental conditions including at least one of temperature, pressure, and concentration of at least one component of the treatment gas.

15. A method of isolating and treating an item, the method comprising:

assembling an enclosed assembly around an item receiving region in which the item is to be isolated and treated, the enclosure assembly including flexible panels each including an inner layer and an outer layer which define an interior wall space therebetween and a connection assembly which includes:

a rigid panel support mounted on the enclosed assembly;
a first gas connector mounted through the rigid panel and sealed thereto for conveying gas into the inner wall space, the first gas connector having a fitting on the outside for connection with a source of gas,
a second gas connector mounted through the rigid panel and sealed thereto for conveying gas into the item receiving region, the second fluid connector having a fitting on the outside for connection with a source of an antimicrobial treatment gas, and
an electrical connector mounted through the rigid panel and sealed thereto providing electrical power to the item receiving region, the electrical fitting having a quick connect electrical coupling on the outside for connection with an electrical source and a quick connect coupling on the inside for connection to an electrical device;
connecting a source of pressuring gas to the first gas connector outside fitting for conveying fluid into the interior wall space;
supplying gas at a positive pressure to a first gas connector to pressurize the interior wall space;
connecting electrical power with the electrical connector outside quick connected coupling;
connecting a source of the antimicrobial treatment gas to the second gas connector outside fitting;
connecting an electrical device located in the receiving region with the electrical connector inside quick connect coupling;
conveying the antimicrobial gas into the item receiving region to treat an item in the item receiving region with the antimicrobial treatment gas.

16. The method of claim 15, further comprising:

one of heating and cooling the gas for pressurizing the interior wall space before the pressurizing gas enters the interior wall space to control temperature in the item receiving region.

17. The method of claim 15, further including:

a third gas connector mounted in the rigid panel for passing the treatment gas out of the flexible enclosure and the method includes removing treatment fluid from the enclosure via the third gas connector.

18. The method of claim 17, wherein the electrical device includes a fan disposed in the item receiving region and further including:

circulating the treatment gas around the item receiving region with the fan;
propelling the treatment gas throughout the enclosure and into difficult to access portions of the item.

19. A walk-in enclosure assembly comprising:

a portable framework that is assembled from poles and connecting pieces to define a treatment region;
a flexible enclosure hung on the framework to define, with a floor, a substantially air fight enclosure around the treatment region;
a door defined in the flexible enclosure to provide walk-in access to the treatment region;
a rail type zipper which seals the door in a closed position;
a rigid support panel mounted to at least two poles of the framework, the support panel carrying:
a first fluid connection which selectively connects a decontaminant fluid supply conduit exterior to the enclosure, with a fluid supply passage for supplying decontaminant fluid to the treatment region,
a second fluid connection through which used treatment fluid is discharged from the treatment region, and
an electrical power connection which selectively connects an electrical power supply with electrical equipment placed in the enclosure.

20. The enclosure assembly of claim 19, wherein the flexible enclosure is transparent.

21. The enclosure assembly of claim 19, wherein the enclosed space is defined, in part, by a floor surface which supports the item to be treated and the framework and further including flaps extending from the flexible enclosure, the flaps being configured for being sealed to the floor surface.

22. The enclosure assembly of claim 19, wherein the flexible enclosure includes an inner layer and an outer layer which define an interior wall space therebetween and further including a third fluid connection mounted to the rigid panel, the third fluid connection having a quick coupling on the exterior rigid panel and discharging into the interior wall space.

23. The enclosure assembly of claim 22, further comprising:

a decontaminant gas source connected with the decontaminant supply conduit;
a source of pressurizing gas different from the decontaminant gas source fluidly connected the second fluid connection quick connect coupling to supply a pressurizing gas under positive pressure to the interior wall space.

24. A decontaminant system comprising:

a portable framework;

a flexible enclosure hung on the framework which defines at least a part of an enclosed decontamination space, the enclosure having a double wall construction which defines an interior wall space isolated from the enclosed decontamination space;

a source of a microbial decontaminant;

a first fluid flowpath fluidly connecting the source of microbial decontaminant fluid with the enclosed space for supplying the enclosed decontamination space with a decontaminant fluid;

a source of pressurizing air different from the microbial decontaminant fluid source which supplies air at a higher pressure than the source of microbial decontaminant;

a second fluid flow path different from the first fluid flow path which supplies the pressurizing air to the interior wall space such that pressure in the interior wall space is maintained higher than pressure in the enclosed decontamination region to help prevent microbial decontaminant fluid from escaping from the enclosed decontamination space into ambient atmosphere.

25. The enclosure assembly of claim 24, further comprising:

a temperature element which selectively heats or cools the gas before entering the interior wall space in accordance with treatment region temperature.

26. The decontaminant system of claim 24, wherein the fluid flowpath includes:

a fluid conduit exterior to the enclosure which is fluidly connected with the source of decontaminant fluid;

a fluid supply passage, which enters the enclosure, a quick connect connector, mounted to the framework, for selectively fluidly connecting and disconnecting the fluid conduit and the fluid supply passage.

27. The decontaminant system of claim 24, wherein the source of microbial decontaminant fluid includes:

a reservoir containing a liquid;

a vaporizer for vaporizing the liquid to form the microbial decontaminant fluid; the system further comprising:

a source of carrier gas for mixing with the vaporized microbial decontaminant and transporting the vaporized microbial decontaminant to the enclosure.

28. The decontaminant system of claim 27, further comprising a cart which is movable relative to the framework and the flexible enclosure, at least one of the reservoir, vaporizer and source of carrier gas being mounted on the cart.

29. The decontaminant system of claim 24, wherein the enclosure is configured for maintaining a positive pressure such that when air at a pressure equivalent to about 3.81 cm water is supplied to the enclosed decontamination space, the enclosure maintains a pressure equivalent to at least 2 cm water in the enclosed decontamination space for at least five minutes after the air supply is disconnected.

30. The decontaminant system of claim 24, further including:

a fluid exhaust flowpath, connected with the enclosure, through which spent microbial decontaminant fluid exits the enclosure.

31. The decontaminant system of claim 24, further including:

a circulation means, disposed within the enclosure, for circulating the microbial decontaminant throughout the enclosed space.

32. The decontaminant system of claim 31, further including:

a support panel mounted to the framework which carries an electrical connection fitting for connecting electrical power from outside the enclosure to the treatment region and the circulation means includes a fan in the enclosure which receives electrical power through the electrical connection fitting.

33. A decontaminant system comprising:

a source of decontaminant gas;

a portable framework;

a flexible enclosure hung on the framework which defines at least a part of an enclosed space;

a rigid support panel mounted to and directly supported by the framework, the support panel carrying:

a first gas connection fitting which selectively connects a gas supply conduit from the decontaminant gas source, exterior to the enclosure, with a gas supply passage interior to the enclosure to form a decontaminant gas supply flowpath connecting the source of decontaminant gas with the enclosed space for supplying the enclosed space with a decontaminant gas; and a second gas connection fitting which selectively connects a gas passage, connected with the enclosure, with an outlet conduit to form the gas exhaust flowpath.

34. The decontaminant system of claim 33, wherein the rigid support panel supports an electrical connection fitting for selectively connecting a sensor within the enclosure with monitoring means outside the enclosure.

* * * * *